(12) United States Patent
Richard et al.

(10) Patent No.: US 9,788,552 B2
(45) Date of Patent: Oct. 17, 2017

(54) USE OF A NATURAL GRAPE MARC EXTRACT IN ORDER TO STIMULATE THE NATURAL DEFENSES OF PLANTS

(75) Inventors: Claire Richard, Beaumont (FR); Alexandra Ter Halle, Lezoux (FR); Pascale Goupil, Perignat-les-Sarlieve (FR); Gerard Ledoigt, Romagnat (FR); Boris Eyheraguibel, Romagnat (FR); Denis Thiery, Sadirac (FR)

(73) Assignees: CENTRE NATIONAL DE LA RECHERCHE SCIENTIFIQUE—CNRS, Paris (FR); UNIVERSITE BLAISE PASCAL CLERMONT FERRAND II, Clermont Ferrand (FR); INSTITUT NATIONAL DE LA RECHERCHE AGRONOMIQUE, Paris (FR)

( * ) Notice: Subject to any disclaimer, the term of this patent is extended or adjusted under 35 U.S.C. 154(b) by 62 days.

(21) Appl. No.: 13/807,556

(22) PCT Filed: Jul. 1, 2011

(86) PCT No.: PCT/FR2011/051549
§ 371 (c)(1),
(2), (4) Date: Dec. 28, 2012

(87) PCT Pub. No.: WO2012/001329
PCT Pub. Date: Jan. 5, 2012

(65) Prior Publication Data
US 2013/0109571 A1 May 2, 2013

(30) Foreign Application Priority Data
Jul. 2, 2010 (FR) ...................... 10 55397

(51) Int. Cl.
*A01N 65/00* (2009.01)
*A01N 65/08* (2009.01)

(52) U.S. Cl.
CPC ............. *A01N 65/00* (2013.01); *A01N 65/08* (2013.01)

(58) Field of Classification Search
CPC ................................ A01N 65/00; A01N 65/08
USPC ........................................................ 424/189
See application file for complete search history.

(56) References Cited

FOREIGN PATENT DOCUMENTS

| EP | 2189062 A1 | 5/2010 |
|---|---|---|
| WO | WO 03/086079 A2 | 10/2003 |
| WO | 2004062370 | 7/2004 |
| WO | 2010060528 | 6/2010 |

OTHER PUBLICATIONS

Kammerer, D., Recovery of anthocyanins from Grape Pomace Extracts (Vitis vinifera L. cv. Cabernet Mitos) using a Polymeric Adsorber Resin, 2005, Eur. Food. Res. Technology, vol. 220, pp. 431-437.*
International Search Report dated Mar. 21, 2012 in corresponding application PCT/FR2011/051549.
Kavroulakis et al, Local and systemic resistance against fungal pathogens of tomato plants elicited by a compost derived from agricultural residues, Physiological and Molecular Plant Pathology, Academic Press LTD, GB, May 1, 2005, pp. 163-174, vol. 66.
Ntougias et al, Suppression of soil-borne pathogens of tomato by composts derived from agro-industrial wastes abundant in Mediterranean regions, Biology and Fertility of Soils: Cooperating Journal of International Society of Soil Science, Springer, Berlin, DE, Jun. 4, 2008, pp. 1081-1090, vol. 44.
Aziz, A, et al., "Laminarin Elicits Defense Responses in Grapevine and Induces Protection against Botrytis cinerea and Plasmopara vitcola," 2003, pp. 1118-1128, vol. 16(12), The American Phytopathological Society.
Notice of Opposition for European Application No. EP 11741629.7, dated Sep. 2, 2015, 16 pages.

* cited by examiner

*Primary Examiner* — John Pak
*Assistant Examiner* — Andriae M Holt
(74) *Attorney, Agent, or Firm* — RatnerPrestia

(57) ABSTRACT

The invention relates to the use of a grape marc extract in order to stimulate the natural defenses of plants and to a method for stimulating the natural defenses of plants, which comprises the application on said plants of a composition comprising a grape marc extract.

11 Claims, 6 Drawing Sheets

USE OF A NATURAL GRAPE MARC EXTRACT IN ORDER TO STIMULATE THE NATURAL DEFENSES OF PLANTS

Increasing the yields is a central concern of farmers. However, yields depend largely on the good development of the plant and consequently on its growth, as well as its good health.

Plant growth is directly related to the absorption and assimilation of inorganic elements as well to the release of hormones governing the elongation and differentiation of plant tissues. Consequently, nutrients and hormones play an essential role in plant growth. Due to their inability to move, plants have developed active and activatable mechanisms enabling them to best use the resources present to promote their growth. Fertilizers are used in order to increase this growth. It is also possible to use other molecules, often glucidic, extracted from algae to promote growth.

The integrity of the plants is also an essential condition for ensuring yield. However, plants are constantly subjected to attack by pathogenic microorganisms. Establishing defenses is thus a decisive factor in terms of resistance effectiveness.

Conventionally, potentially toxic phytopharmaceutical products are used on a mass scale to defend against attack by pathogens.

The products arising from the agro-pharmaceutical industry (fungicides, insecticides) marketed by agrochemical firms have a significant impact on the environment with potential toxicities for man.

The artificial induction of plant defense mechanisms against parasites is the focus of much research. The first research approach, consisted in finding molecules that mimic the action of salicylic acid, which is capable of inducing in itself alone an immunity but which is insufficiently tolerated by certain plants. A chemical analog of salicylic acid, INA (or 2,6-dichloroisonicotinic acid), and other synthesis elicitors have been developed: benzothiadiazole (BTH, marketed by SYNGENTA under the BION® brand) and β-aminobutyric acid (BABA®-Sigma Aldrich), which are better tolerated by crop plants.

The second approach has consisted in seeking natural molecules (oligosaccharides, enzymatic proteins, polypeptides) capable in themselves alone of inducing plant defense mechanisms.

Fungal extracts from *Fusarium* (WO/2002/24869) and from *Trichoderma* (WO/2006/129998) have shown natural plant defense-stimulating properties.

Microorganism extracts from *Erwinia* (WO/1998/37752, WO/1999/07206), *Xanthomonas* (WO/2000/20616), *Agrobacterium* (WO/2000/28056), *Cladosporium* (WO/2002/02787), Gram-positive bacteria (WO/1999/11133) and *Pseudomonas* (WO/1999/07207, WO/2003/068912) have the ability to induce natural plant defenses (Varnier 2009). Extracts from insects and shellfish containing β-1,3-glucans (chitosan) have shown natural plant defense-stimulating properties (Klarzynski 2000). The ELEXA® formulation (SAFE SCIENCE), whose active ingredient is chitosan, is marketed as an elicitor (Sharathchandra 2004).

Yeast extracts have natural plant defense-stimulating properties (A1/2009/0010905).

Brown algae extracts containing an oligosaccharide called laminarin induce plant defense reactions (Aziz 2003, EP 1 338 200 and WO/2005/082150). GOEMAR markets the "Iodus® 2 cereals" and "Iodus 2 specialised crops" formulations whose active ingredient is laminarin.

Many plant extracts have defense-stimulating properties. Fenugreek (*Trigonella foenum greacum*) seed extracts may be used to activate defense reactions (WO02102162 and WO0410786). The STIFENIA formulation (SOFT) is marketed as a natural elicitor.

Aqueous neem tree (*Azadirachta indica* Juss.) leaf extracts containing tetranortriterpenoids (Paul 2002), ethanolic extracts of leaves of the giant knotweed (*Reynoutria sachalinensis*) (Daayf 1997; Randoux 2006), extracts of bouqainvillea leaves (Narwal 2000), of rhubarb and of spinach (Doubrava 1988) have shown a plant defense reaction-eliciting effect. The MILSANA formulation (SCHAETTE) containing giant knotweed extracts is marketed as a natural elicitor. WO/2003/086079 describes the use of an ethanolic extract of vine leaves.

Extracts of rhubarb (*Rheum palmatum*) root and of alder buckthorn (Frangula alnus) bark have a potential to elicit vine defense mechanisms (Godard 2009).

Other plant extract-based formulations are awaiting authorization for sale as elicitors: Pireco (mixture of 11 extracts of plants including soy and marine algae) from TEAM GREEN; Echo Protect (mixture of natural extracts of plants including nettle, garlic). Kavroulakis et al., in Physiological and Molecular Plant Pathology, Academic Press Ltd, GB, vol. 66, no. 5, pp. 163-174, and Spyridon Ntougias et al., in Biology and Fertility of Soils; Cooperating Journal of International Society of Soil Science, Springer, Berlin, vol. 44, no. 8, pp. 1081-1090, have worked on the use of composts, i.e. biodegraded plant waste, as elicitors.

The effectiveness of these formulations is often partial, specific to certain plant varieties, or in the developmental stage. They generally have to be combined with chemical treatments. Moreover, some compounds do not cause resistance several times in succession (fenugreek plant extracts); a single spraying is possible. Their preventive and/or curative action may be limited over time.

There thus exists a need for a composition that is respectful of the environment and of the plants for which it is intended and that stimulates their pathogen-defense system. The present inventors have found that a natural grape marc extract has such an activity. The proposed extract thus has the ability to stimulate the defense mechanisms of treated plants.

BRIEF DESCRIPTION OF DRAWINGS

FIG. 3 is a graph showing the relative quantity of the expression of SAR response marker gene pr1 in leaves of the same plants, each leaf being treated differently.

Figure 1A:
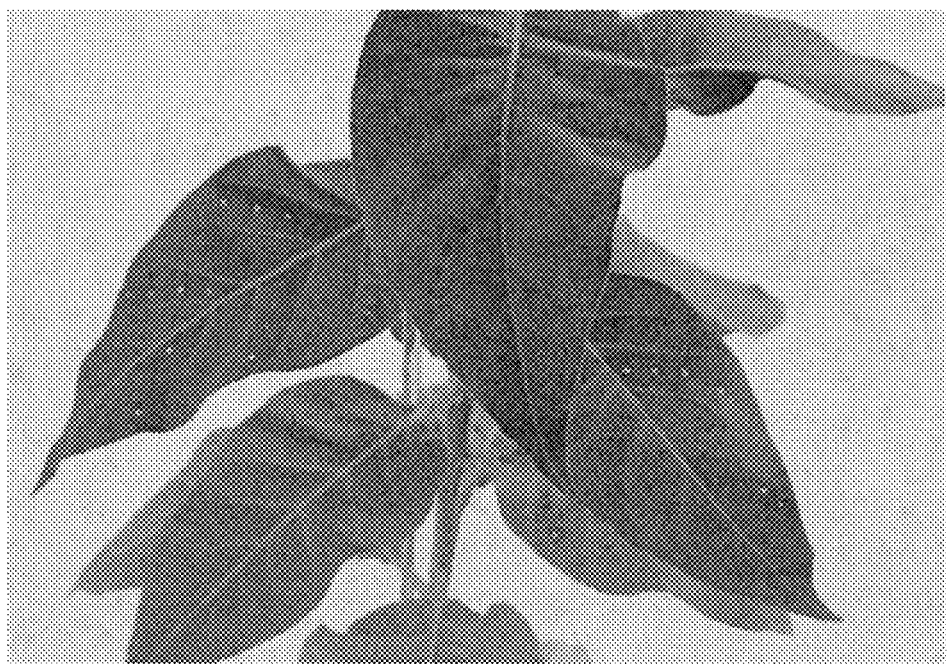
FIG. 1a is a photograph of tobacco seedling leaves infiltrated with grape marc extract taken just after infiltration.

Thus, the invention relates to the use of a grape marc extract in order to stimulate the natural defenses of plants. Grape marc consists of the solid remains after the pressing of grapes, i.e. skins, seeds and possibly stalks. Grape marc thus results from the physical transformation of grapes. The grape marc extract has not undergone composting.

The grape marc extract whose use is proposed makes it possible to induce the expression of defense genes, i.e. to stimulate the natural defenses of plants. As a result, it has elicitation properties.

According to one embodiment, the grape marc extract, whose use is the subject matter of the present invention, includes natural compounds which are synthesized by the grape itself, whose cultivation is widespread, and which are obtained by a conventional method (non-industrial). These compounds thus have a much better chance of being well tolerated and having nontoxic effects. Finally, these natural compounds may be used in organic farming.

These natural compounds are notably polyphenols and anthocyanins. The extract used according to the invention may contain more than 70% polyphenols by weight in relation to its dry weight. The extract may also include more than 8% anthocyanins by weight in relation to the dry weight of the extract.

The grape marc extract used according to the invention can be prepared from red grape marc to which water is added and which undergoes centrifugation. The centrifugation product is then extracted in a water-ethanol mixture containing less than 30% (v/v) ethanol, and then is concentrated under vacuum and atomized with no drying support, so as to obtain a powder. The process is carried out in the presence of $SO_2$, with no addition of additive. The sulfite added to the diffusion water, at a concentration of about 1 g/l, has the role of solubilizing the anthocyanins and limiting their oxidation.

The natural compounds present in the grape marc extract are compounds that are easy to extract, inexpensive and water-soluble and thus easy to use (easy dilution). They may improve the properties of formulants accompanying the active ingredients due to their photoprotective role.

The use according to the invention is completely suitable for plants selected from the group consisting of agronomically useful plants and ornamental plants.

Agronomically useful plants are selected from the group of the angiosperms comprising the Apiaceae, the Asteraceae, the Brassicaceae, the Chenopodiaceae, the Convolvulaceae, the Cucurbitaceae, the Fabaceae, the Liliaceae, the Polygonaceae, the Rosaceae, the Solanaceae, the Poaceae and the Vitaceae, The invention also relates to a method for stimulating the natural defenses of plants, which includes the application on said plants of a composition including a grape marc extract.

The composition used in the method according to the invention includes, as active product, an aqueous/alcoholic extract of grape marc. The grape marc extract includes more than 45%, preferably more than 70%, polyphenols by weight in relation to the dry weight of the extract, The extract includes more than 0.5%, preferably more than 8%, anthocyanins by weight in relation to the dry weight of the extract. The grape marc extract is advantageously obtained according to the method described above.

The composition used in the method according to the invention may foe provided in powder form or in liquid form.

When the composition is provided in the powder form, it is free of any other active agent.

It may also be free of any non-natural adjuvant.

According to a particular embodiment of the method according to the invention, the composition is an aqueous composition that is applied by foliar spraying or by infiltration.

The concentration of grape marc extract in the composition used in the method according to the invention is between 0.10 g/l and 10 g/l, preferably between 0.3 g/l and 2.5 g/l, more preferentially still between 0.5 g/l and 1.25 g/l, for application by spraying with a view to promoting natural plant defenses. A single application before attack by pathogens may suffice. However, it may prove necessary at times to repeat the application at least once several days or several weeks after the first.

The composition is applied at a concentration of 0.1 to 2.0 kg/ha, preferably 0.3 to 1.5 kg/ha, of crops to be treated to promote natural defenses.

Application doses and protocols, of course, depend on the plant species to be treated and to its stage of development.

According to a particular embodiment, infiltration of the grape marc extract takes place at a concentration of less than 0.30% (w/v), preferably 0.05% to 0.30% (w/v).

The method according to the invention may be implemented on agronomically useful plants and on ornamental plants. Such plants are those mentioned above in connection with the use.

The infiltration of a grape marc extract at a concentration of 0.25% on tobacco leaves induces a hypersensitive response (local) accompanied by a systemic resistance response (SAR: systemic acquired resistance), expressing the elicitor effect of the extract, an effect characteristic of the induction of immunity vis-à-vis pathogens. This elicitor effect has been demonstrated at the molecular level by analysis of the expression of marker genes for the SAR response (pr1 and pr2 ).

The elicitor effect of a grape marc extract has also been demonstrated for other dicotyledons (tomatoes) and for monocotyledons (corn).

Use of this extract will enable a reduction in the quantity of pesticides used to protect plants from pathogens. In organic farming, use of this extract will enable a reduction in pesticides.

The invention will be described below in greater detail using the following examples which are given for illustrative purposes only.

The experiments were carried out on transcripts isolated from plants treated with grape marc extract, from plants treated with salicylic acid (SA) (positive control, SA is a known elicitor of the SAR response) and from plants sprayed without elicitor (water, negative control), PR gene expression is analyzed by semi-quantitative real-time PCR enabling the amplification of transcripts of interest. The results show an accumulation of transcripts in plants treated with the extracts, which suggests an elicitor-type response of our plant extracts.

EXAMPLES

In the following examples, the product marketed by GRAP'SUD under the brand exGrape® Anthocyanins is used as the grape marc extract. This product has the following characteristics:
slightly granulated dark-red powder
total polyphenols:
(in catechin equivalents) OD 280 nm: ≥70%
(in gallic acid equivalents) Folin-Ciocalteu: ≥60%
procyanidins:
(in catechin equivalents) Vanillin assay: ≥5%
anthocyanins:
Bisulfite bleaching: ≥8%
In the examples, this product is called "EXTRACT".
A β-aminobutyric acid potentiator, referred to as BABA in the examples, is also used.

Example 1

Elicitation on Tobacco Leaves

The EXTRACT at 0.25% (w/v) is infiltrated on the leaves of tobacco seedlings at the 10-12 leaf stage (4-5 weeks).

Figure 1B:
FIG. 1b is a photograph of tobacco seedling leaves infiltrated with grape marc extract four days after infiltration.
Figure 1:
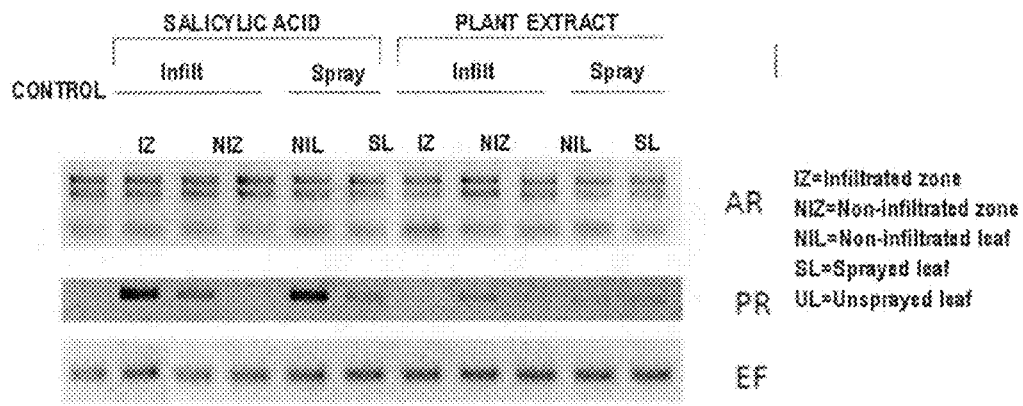

A photograph of the leaves is taken just after infiltration (FIG. 1a), and then 4 days after infiltration: (FIG. 1b). Four days after infiltration, the hypersensitive response is observed on the leaves that were pricked.

A salicylic acid control (2 mM) is prepared and the SAR response is analysed by real-time PCR.

Figure 2:
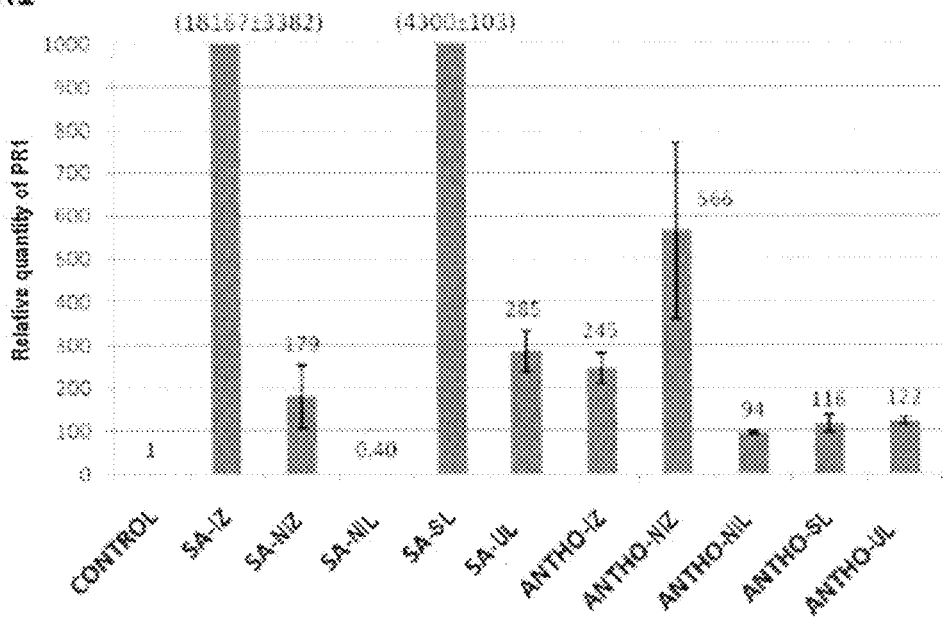
FIG. 2 shows an accumulation of transcripts in seedlings treated with the extracts.
Figure 4:
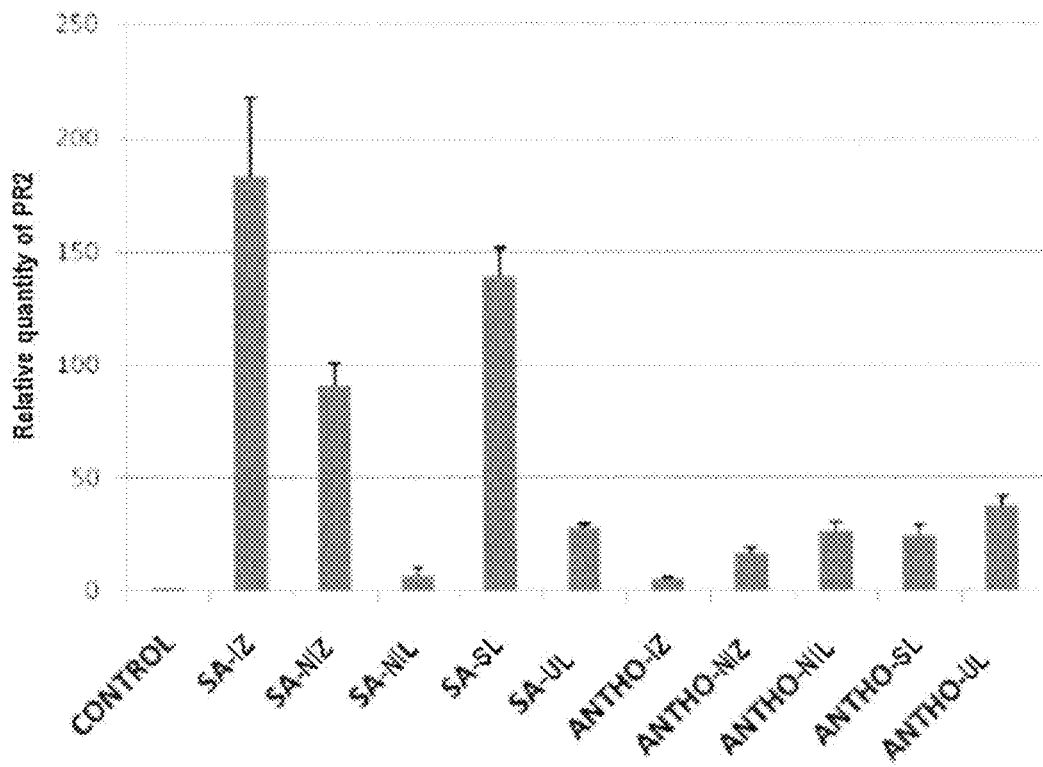
FIG. 4 is a graph showing the relative quantity of the expression of SAR response marker gene pr2 in different leaves of the same plants, each leaf being treated differently.

The results obtained are presented in FIGS. 2, 3 and 4.

These results show an accumulation of transcripts in seedlings treated with the extracts, in the infiltrated or sprayed leaves and the unsprayed or non-infiltrated leaves of the same treated plant, which suggests an elicitor-type response of the EXTRACT.

This elicitor effect was shown at the molecular level by analysis of the expression of SAR response marker genes (pr1 and pr2).

The molecular analysis consisted in extracting total RNA from treated tobacco leaves using the Tri-reagent extraction kit (Euromedex). The integrity of the extracted RNA is verified by agarose gel electrophoresis. Euroscript (Eurogentec) reverse transcriptase (RT) is used for the synthesis of complementary Dish. Primers (20- to 24-mer oligonucleotides) specific for the pr1 and pr2 genes enabled amplification of the corresponding cDNA by polymerase chain reaction (PCR). Amplification is monitored in real-time (real-time PCR) based on the fluorescence emitted by the amplification products in the presence of SYBR Green. The specific pr1 and pr2 RT-PCR fragments are quantified using the iQv3 software (BIO-RAD). The abundance of pr1 and pr2 transcripts is standardized (relative quantity) with those of a constitutive expression gene, coding for actin or elongation factor alpha.

Example 2

The same tests are repeated with various concentrations of EXTRACT: 2.5 g/l, 1.25 g/l, 0.625 g/l, 0.312 g/l and 0.156 g/l, and various quantities sprayed per leaf and per seedling. This is done in order to determine the final quantity that enables elicitation.

Figure 5:
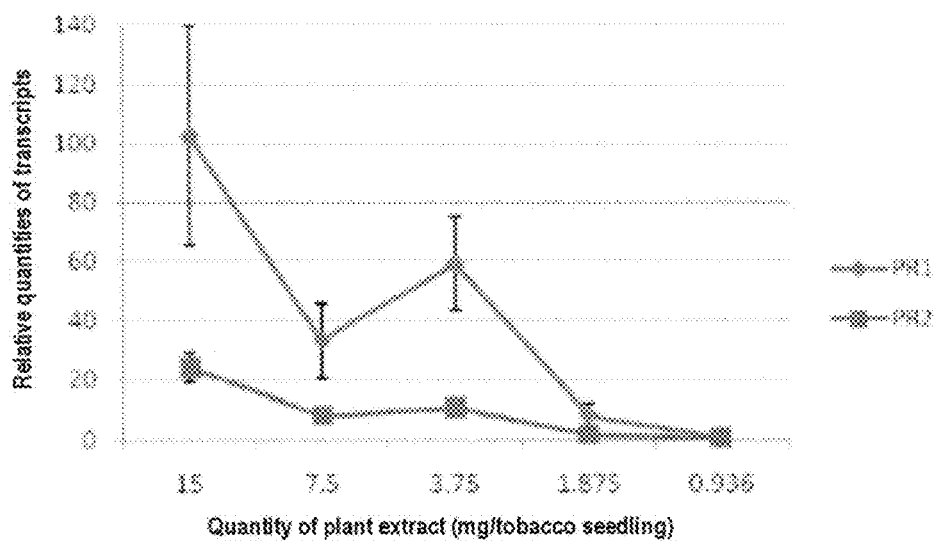
FIG. 5 is a graph showing the relative quantity of the expression of SAR response marker genes pr1 and pr2 in relation to the quantity of plant extract.

The quantities used are presented in the following table and the results are given in FIG. 5.

|  | Dilution from the 1% EXTRACT stock solution | | | | |
| --- | --- | --- | --- | --- | --- |
|  | X4 | X8 | X16 | X32 | X64 |
| EXTRACT concentration | 2.5 g/l | 1.25 g/l | 0.625 g/l | 0.312 g/l | 0.156 g/l |
| Quantity sprayed/leaf | 5 mg | 2.5 mg | 1.25 mg | 0.625 mg | 0.312 mg |
| Quantity sprayed/seedling | 15 mg | 7.5 mg | 3.75 mg | 1.875 mg | 0.936 mg |

Example 3

Various tobacco leaf infiltration tests were carried out with 50 µl of solution as follows:
Test 1: 0.25% (w/v) EXTRACT
Test 2: 0.125% (w/v) EXTRACT
Test 3: 0.0625% (w/v) EXTRACT
Test 4: 0.03125% (w/v) EXTRACT
Test 5: 0.0156% (w/v) EXTRACT
Test 6: 10 mM BABA
Test 7: (positive control): 2 mM salicylic acid
Test 8: (negative control): water Eight days after infiltration, macroscopic symptoms were observed under white light and under UV light (wavelength=312 nm). The corresponding photographs are presented in FIGS. 6 and 7. In the figures, the numbers correspond to the spot of infiltration of the test of the same number.

Figure 6:
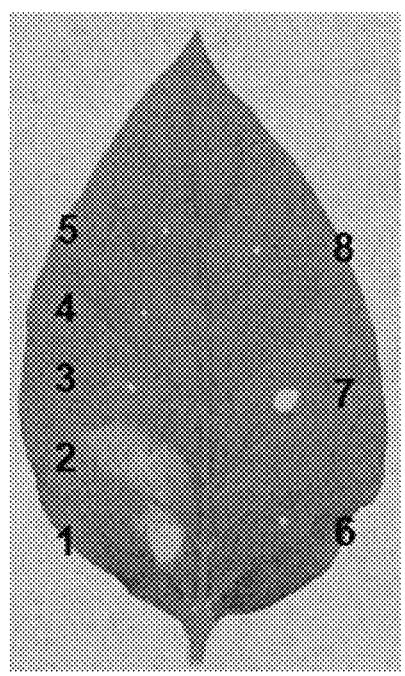
FIG. 6 is a photograph under white light of tobacco seedling leaves infiltrated with grape marc extract taken eight days after infiltration.
Figure 7:
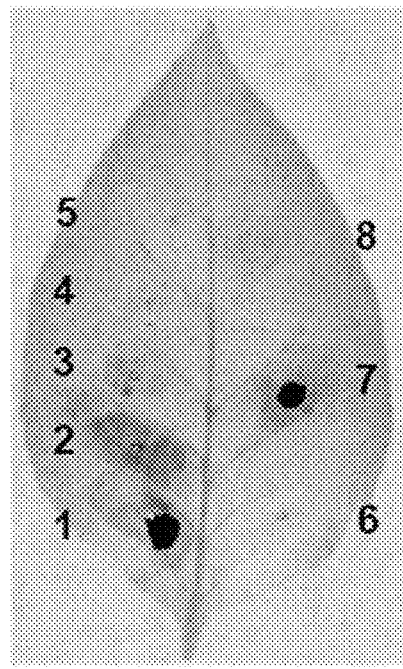
FIG. 7 is a photograph under UV light of tobacco seedling leaves infiltrated with grape marc extract taken eight days after infiltration.

It is seen in these photographs that the grape marc extract induces chlorosis (light area lacking chlorophyll) in infiltrated tissues (1 and 2 in FIG. 6) with the appearance of necrosis (dried brown area) when the extract is used at a high concentration (1 in FIG. 6).

BABA (10 mM) (6 in FIG. 6), due to its potentiator effect, and water (8 in FIG. 6) do not induce chlorosis or necrosis at the infiltrated sites. Salicylic acid (2 mM) (7 in FIG. 6) causes necrosis in infiltrated foliar tissues.

The grape marc extract infiltrated at concentrations of 0.25% (1), 0.125% (2) and 0.0625% (3) in tobacco leaves induces a local accumulation of fluorescent compounds (1, 2 and 3 in FIG. 7) characteristic of local acquired resistance (LAR) intervening in plant defense reactions.

Example 4

An Evans Blue assay is carried out on the infiltrated leaves of example 3. Evans Blue is a vital dye that easily penetrates a cell when the cell's plasma membrane is damaged and permeable. It thus shows the loss of cell integrity when there is cell death in the hypersensitive response.

Discs of leaf (1 cm in diameter) punched out around the infiltration point are incubated in Evans solution (0.25%) at room temperature and with moderate agitation for 30 minutes for satisfactory penetration of the dye into the cells. The leaf discs are carefully washed with distilled water and then ground in the presence of 1 ml of 0.1% SDS until complete homogenization is achieved. The homogenate is centrifuged for 20 minutes at 20,000×g and the supernatant is diluted 8 times with distilled water. The optical density is measured at 600 nm and based on the weight of fresh material.

Figure 8:
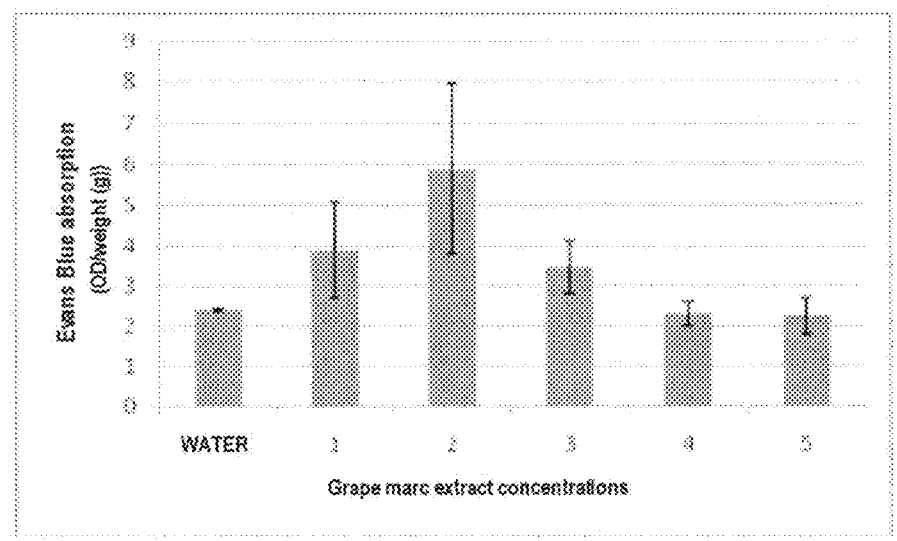
FIG. 8 is a graph showing the Evans blue absorption on infiltrated leaves in relation to the grape marc extract concentration.

The results are presented in the graph in FIG. 8.

The foliar tissues infiltrated by the grape marc of tests 1, 2 and 3 exhibit greater absorption of Evans Blue than that of the control water (test 8), suggesting the initiation of cell death.

This reaction is characteristic of the hypersensitive response intervening in plant defense reactions.

Example 5

Tomato leaves and corn leaves were infiltrated with 50 µl of water (negative control), on the one hand, and 50 µl of 0.25% (w/v) EXTRACT, on the other hand.

Figure 9:
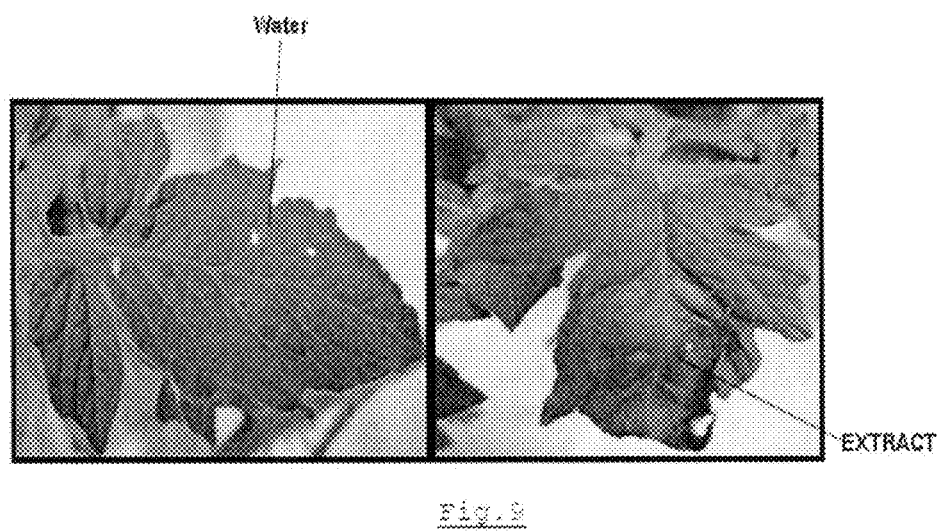
FIG. 9 is a photograph under white light of tomato leaves four days after infiltration.
Figure 10:
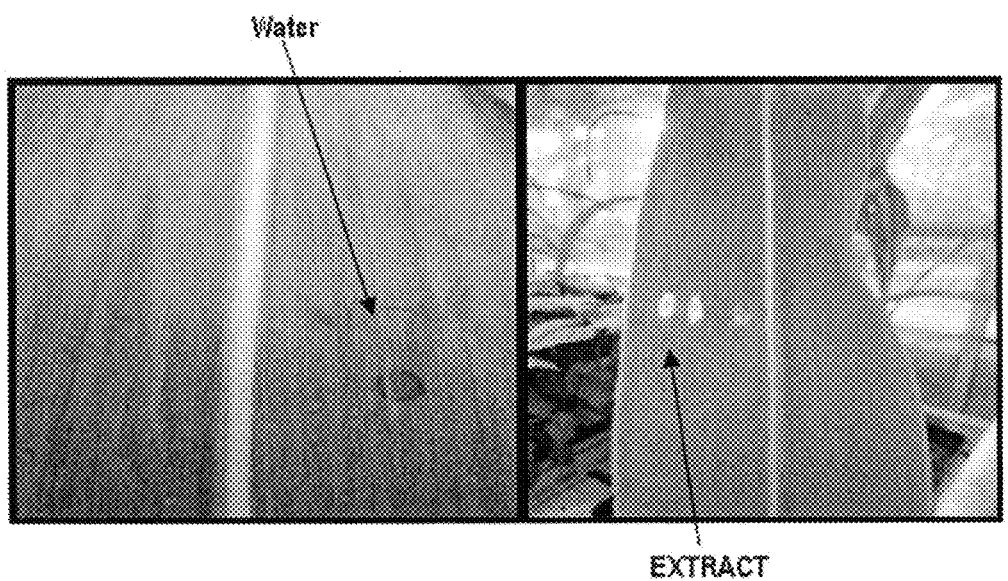
FIG. 10 is a photograph under white light of corn leaves four days after infiltration.

Four days after infiltration, photographs were taken under white light. These photographs are presented as FIG. 9 for tomato and as FIG. 10 for corn.

In these figures, it is seen that the grape marc extract infiltrated at 0.25% (50 µl) induces a hypersensitive response (necrosis) in tomato (a dicotyledon) and in corn (a monocotyledon).

REFERENCES

Aziz et al. (2003), Laminarin elicits defense responses in grapevine and induces protection against Botrytis cinerea and Plasmopara viticola. MPMI, 16(12):1118-1128.

Daayf, F., Schmitt, A., Belanger, R. R., 1997. Evidence of phytoalexins in cucumber leaves infected with powdery mildew following treatment with leaf extracts of Reynoutria sachalinenesis. Plant Physiol., 113, 719-727.

Doubrava, N. S., Dean, R. A., Kuc, J., 1988. Induction of systemic resistance to anthracnose caused by *Colletotrichum lagenarium* in cucumber by oxalate and extracts from spinach and rhubarb leaves. Physiol. Mol. Plant Pathol., 33, 69-79.

Klarzynski et al. (2000). Linear b-1,3-glucans are elicitors of defense responses in tobacco. Plant Physiol., 124:1027-1037.

Godard et al. (2009). Induction of defence mechanisms in grapevine leaves by emodin- and anthroquinone-rich plant extracts and their conferred resistance to downy mildew. Plant Physiology and Biochemistry, 47, 827-837.

Narwal et al. (2000). A systemic resistance inducing antiviral protein with N-glycosidase activity from Bougainvillea xbuttiana leaves. Indian J. Exp. Biol., 39, 600-603.

Paul and Sharma (2002). *Azadirachta indica* leaf extract induces resistance in barley against leaf stripe disease. Physiological and Molecular Plant Pathology, 61, 3-13.

Randoux at al, (2006). Inhibition of *Blumeria graminis* f. sp. Tritici germination and partial enhancement of wheat defenses by Milsana. Biochemistry and Cell Biology, 96, 1278-1286.

Sharathchandra et al. (2004). A chitosan formulation Elexa™ induced downy mildew disease resistance and growth promotion in pearl millet. Crop Protection, 23:381-888.

Tosun et al. (2003). The effect of HarpinEa as plant activator in control of bacterial and fungal diseases of tomato. Congrès Acta horticulturae, 2003, no. 616, pp. 251-254

Varnier et al. (2009). Bacterial rhamnolipids are novel MAMPs conferring resistance to *Botrytis cinerea* in grapevine. Plant, Cell and Environment, 32, 178-193.

The invention claimed is:

1. A method of inducing natural defenses in a plant, comprising applying to said plant, prior to exposure of the plant to a pathogen, a composition comprising an elicitor, wherein the elicitor is grape marc extract that has not undergone composting, and wherein the method induces a hypersensitive response in the plant prior to exposure of the plant to a pathogen, wherein the plant is a tobacco plant, a tomato plant or corn, and wherein the quantity of grape marc extract is from 0.0625% to 0.25% (w/v).

2. The method of claim 1, wherein the composition is an aqueous composition and it is applied by foliar spraying or by infiltration.

3. The method of claim 1, wherein the extract includes more than 45% polyphenols by weight in relation to the dry weight of the extract.

4. The method of claim 1, wherein the extract includes more than 70% polyphenols by weight in relation to the dry weight of the extract.

5. The method of claim 1, wherein the extract includes more than 0.5% anthocyanins by weight in relation to the dry weight of the extract.

6. The method of claim 1, wherein the extract includes more than 8% anthocyanins by weight in relation to the dry weight of the extract.

7. The method of claim 3, wherein the composition comprises an aqueous/alcoholic extract of grape marc.

8. The method of claim 1, wherein the composition is an aqueous mixture comprising grape marc extract corresponding to a concentration of from 0.1 g/L to 10 g/L dry weight of the extract.

9. A method of inducing natural defenses in a plant, comprising applying to said plant, prior to exposure of the plant to a pathogen, a composition comprising an elicitor, wherein the elicitor is grape marc extract that has not undergone composting, wherein the method induces a systemic acquired response in the plant prior to exposure of the plant to a pathogen, wherein the plant is a tobacco plant, a tomato plant or corn, and wherein the quantity of grape marc extract is from 0.0625% to 0.25% (w/v).

10. A method of inducing natural defenses in a plant comprising applying to said plant, prior to exposure of the plant to a pathogen, a composition comprising an elicitor, wherein
   i) the elicitor is grape marc extract that has not undergone composting; and
   ii) the composition is an aqueous mixture comprising grape marc extract corresponding to a concentration of from 0.1 g/L to 2.5 g/L dry weight of the extract;
   and wherein the method induces a hypersensitive response in a plant prior to exposure of the plant to a pathogen, wherein the plant is a tobacco plant, a tomato plant or corn, and wherein the quantity of grape marc extract is from 0.0625% to 0.25% (w/v).

11. A method of inducing natural defenses in a plant, comprising applying to said plant, prior to exposure of the plant to a pathogen, a composition comprising an elicitor, wherein the elicitor is grape marc extract that has not undergone composting, and wherein the method induces a hypersensitive response in the plant prior to exposure of the plant to a pathogen, wherein the plant is a tobacco plant, and wherein the quantity of grape marc extract is from 0.0625% to 0.25% (w/v).

* * * * *